US009894424B2

(12) United States Patent
Propst, Jr. et al.

(10) Patent No.: US 9,894,424 B2
(45) Date of Patent: Feb. 13, 2018

(54) METHOD AND SYSTEM FOR CONVERTING BETWEEN PROTOCOLS

(71) Applicant: Scott Technologies, Inc., Boca Raton, FL (US)

(72) Inventors: Edward R Propst, Jr., Monroe, NC (US); Nicholas Anthony DeBlasio, Monroe, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 0 days.

(21) Appl. No.: 15/125,390

(22) PCT Filed: Mar. 14, 2014

(86) PCT No.: PCT/US2014/027004
§ 371 (c)(1),
(2) Date: Sep. 12, 2016

(87) PCT Pub. No.: WO2015/137958
PCT Pub. Date: Sep. 17, 2015

(65) Prior Publication Data
US 2017/0099527 A1    Apr. 6, 2017

(51) Int. Cl.
*H04Q 9/00* (2006.01)
*G08C 23/04* (2006.01)
(Continued)

(52) U.S. Cl.
CPC .......... *H04Q 9/00* (2013.01); *G01N 33/0004* (2013.01); *G08C 23/04* (2013.01); *H04W 4/22* (2013.01); *H04Q 2209/43* (2013.01)

(58) Field of Classification Search
CPC .......... H04Q 9/00; G08B 21/12; G08B 21/16; G01N 33/0004; H04W 4/22; G01D 4/002
See application file for complete search history.

(56) References Cited

U.S. PATENT DOCUMENTS 6,182,497 B1 *  2/2001  Krajci ............... G01N 33/0075
                                                   340/605
8,620,343 B1 * 12/2013  Lau ......................... G01S 19/09
                                                   340/539.22
(Continued)

FOREIGN PATENT DOCUMENTS

CN        103049984 A     4/2013
KR    1020080064817 A     7/2008
(Continued)

OTHER PUBLICATIONS

International Search Report and Written Opinion dated Dec. 9, 2014, for International Application Serial No. PCT/US2014/027004, International Filing Date—Mar. 14, 2014 consisting of 10 pages.
(Continued)

*Primary Examiner* — Mirza Alam
(74) *Attorney, Agent, or Firm* — Scott Technologies, Inc.

(57) ABSTRACT

In an embodiment a protocol converter module for use with a gas transmitter assembly having a gas sensor, a controller, and a detector transceiver housed within an intrinsically safe detector housing is provided. The controller module comprises a converter housing having a converter mount configured to securely mount the converter module to the detector housing. A controller module includes a first converter transceiver, within the converter housing, configured to bi-directionally exchange data with the detector transceiver utilizing a first protocol. The controller module also includes a second converter transceiver, also within the converter housing, configured to bi-directionally exchange data with an external device using a second protocol. The controller module also include, an electronic converter, also within the converter housing, coupled to the first and second
(Continued)

converter transceivers and configured to convert the data between the first and second protocols.

23 Claims, 6 Drawing Sheets

(51) Int. Cl.
*G01N 33/00* (2006.01)
*H04W 4/22* (2009.01)

(56) References Cited

U.S. PATENT DOCUMENTS

| | | | |
|---|---|---|---|
| 2008/0031206 A1 | 2/2008 | Sharma | |
| 2009/0153357 A1* | 6/2009 | Bushman | G01D 4/008 340/870.02 |
| 2009/0200466 A1 | 8/2009 | Mammen et al. | |
| 2011/0074587 A1* | 3/2011 | Hamm | G06Q 10/0833 340/584 |
| 2011/0140884 A1* | 6/2011 | Santiago | G01S 5/0027 340/539.13 |
| 2011/0248857 A1* | 10/2011 | Rutherford | G08B 21/16 340/632 |
| 2012/0007713 A1* | 1/2012 | Nasiri | G06F 1/1694 340/5.81 |
| 2012/0038458 A1* | 2/2012 | Toepke | G05B 19/042 340/6.1 |
| 2012/0236768 A1 | 9/2012 | Kolavennu | |
| 2013/0147460 A1* | 6/2013 | Blanchard | G01R 31/041 324/66 |
| 2013/0166198 A1* | 6/2013 | Funk | G01C 21/165 701/446 |
| 2013/0179110 A1* | 7/2013 | Lee | A61B 5/1118 702/130 |
| 2013/0274587 A1* | 10/2013 | Coza | A61B 5/6804 600/409 |
| 2015/0163652 A1* | 6/2015 | Michaud | H04W 4/22 370/328 |

FOREIGN PATENT DOCUMENTS

| | | |
|---|---|---|
| WO | 0114873 A1 | 3/2001 |
| WO | 2004/053450 A1 | 6/2004 |
| WO | 2012/016014 A1 | 2/2012 |

OTHER PUBLICATIONS

Extended European Search Report issued by the European Searching Authority dated Dec. 1, 2017 in corresponding European Patent Application No. 14885430.0, consisting of 8 pages.

* cited by examiner

METHOD AND SYSTEM FOR CONVERTING BETWEEN PROTOCOLS

CROSS-REFERENCE TO RELATED APPLICATION

This Application is a Submission Under 35 U.S.C. §371 for U.S. National Stage Patent Application of International Application Number: PCT/US2014/027004, filed Mar. 14, 2014 entitled "METHOD AND SYSTEM FOR CONVERTING BETWEEN PROTOCOLS."

BACKGROUND

The subject matter described herein relates generally to sensing systems and particularly to exchanging data between sensing systems and a handheld communicator.

Environmental sensing systems may include a variety of sensors for detecting the presence and/or concentration of various chemicals in hazardous environments. For example, sensors may be used in hazardous environments for detecting the presence and/or concentration of hazardous (e.g., combustible, volatile, and/or toxic) gases. The environmental sensing system may be required to include intrinsically safe (IS) circuitry to mitigate potential danger from the possibility of combustion resulting from the operation of circuitry in the presence of the hazardous gas.

Handheld communicators may be used to exchange data with the sensing system, for example, to send instructions to the sensing system, and/or to download log files. However, the handheld communicator may not have a communication capability that is compatible with the sensing system. For example, the handheld device may utilize a wired connection using the HART protocol, whereas the sensing system may utilize an optical system based on the IrDA protocol. Additionally, introducing a wired connection in the workspace may require additional. IS circuitry and/or recertification (e.g., declassification and reclassification) of the workspace. Furthermore, the components that comprise the IS circuit (including connection wires) may be required to be partitioned such that the IS components do not directly interact with non-IS components.

SUMMARY

In an embodiment, a protocol converter module for use with a gas transmitter assembly having a gas sensor, a controller, and a detector transceiver housed within an intrinsically safe detector housing is provided. The controller module comprises a converter housing having a converter mount configured to securely mount the converter module to the detector housing. A controller module includes a first converter transceiver, within the converter housing, configured to bi-directionally exchange data with the detector transceiver utilizing a first protocol. The controller module also includes a second converter transceiver, also within the converter housing, configured to bi-directionally exchange data with an external device using a second protocol. The controller module also include, an electronic converter, also within the converter housing, coupled to the first and second converter transceivers and configured to convert the data between the first and second protocols.

In an embodiment, a method of bi-directionally exchanging data with a gas detector assembly and an external device is provided. The method includes securely mounting a protocol converter module to the gas detector assembly using a converter mount. The method includes bi-directionally exchanging data with a detector transceiver housed in the gas detector assembly using a first converter transceiver utilizing a first protocol and bi-directionally exchanging data with the external device using a second converter transceiver utilizing a second protocol. The method includes converting the data between the first and second protocols using an electronic converter communicably coupled to the first and second converter transceivers.

BRIEF DESCRIPTION OF THE DRAWINGS

The drawings, in which like numerals represent similar parts, illustrate generally, by way of example, but not by way of limitation, various embodiments discussed in the present document.

DETAILED DESCRIPTION

Figure 1:
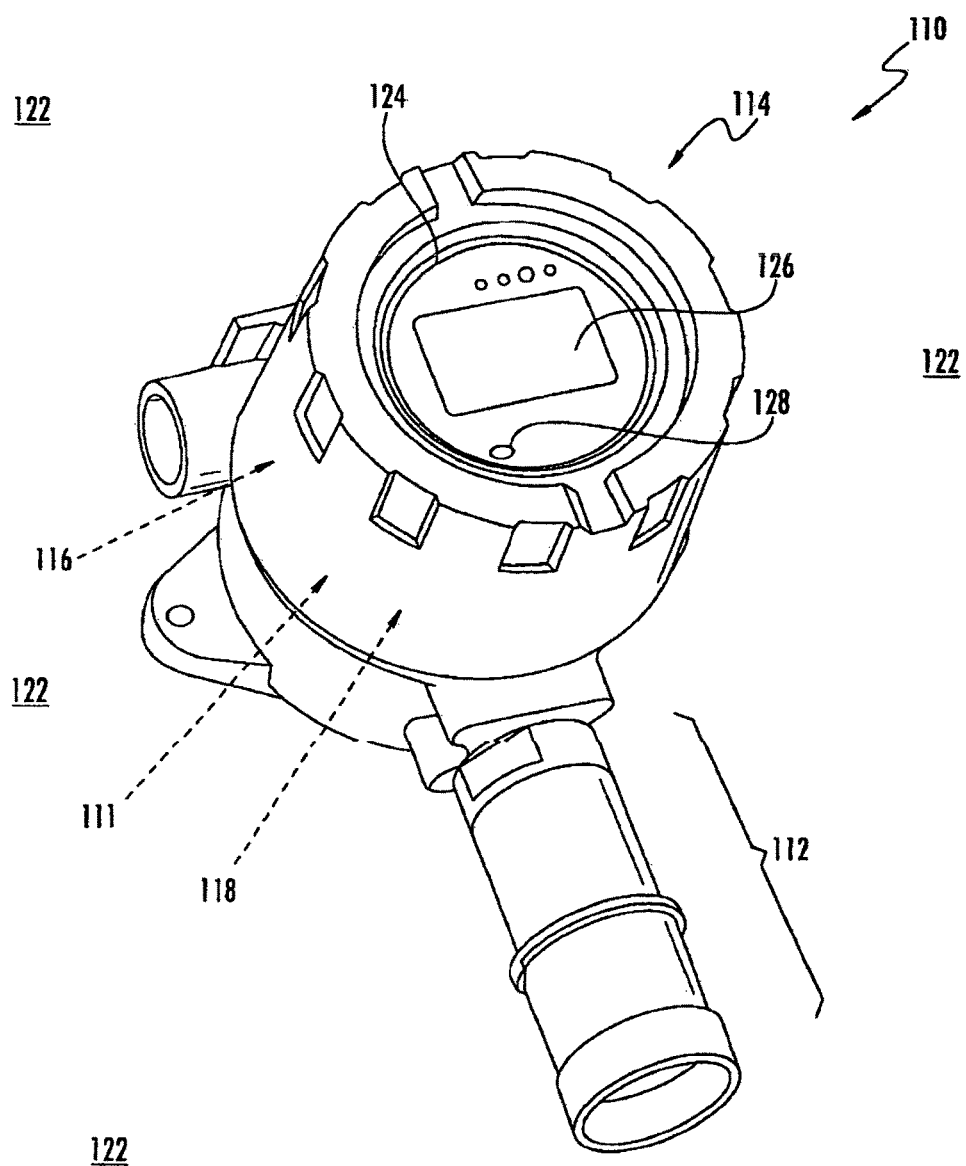
FIG. 1 is a perspective view of an embodiment of a gas detector assembly that may be part of an environmental sensing system.

FIG. 1 is a perspective view of an embodiment of a gas detector assembly 110 that may be part of an environmental sensing system. The gas detector assembly 110 includes a gas sensor 112, and a detector 114. The detector 114 includes a controller 116 and a detector transceiver 118 housed within an intrinsically safe detector housing 120 as is discussed in detail below. The gas sensor 112 is mounted to the detector 114 such that the gas sensor 112 is exposed within an environment 122 for sensing one or more parameters within the environment 122. The gas sensor 112 may be any type of sensor that is configured to sense any parameter(s). The gas sensor 112 provides the parameter(s) to the detector transceiver 118 via the controller 116 housed within the detector 114. As is discussed below, the detector transceiver 118 transmits the parameter(s) upstream to other devices. In some embodiments, the gas sensor 112 is configured to detect the presence and/or amount of a substance (e.g., a volatile gas, a toxic gas, a combustible gas, and/or the like) within the environment 122. Examples of other parameter(s) that may be sensed by the gas sensor 112 include, but are not limited to, pressure, density, temperature, relative humidity, and/or the like.

The gas sensor 112 may be used in any application and the environment 122 may be any environment. In some embodiments, the environment 122 is a hazardous environment, such as, but not limited to, a petroleum well, a power plant, a petroleum pipe system, and/or the like. For example, the gas sensor 112 may be used within a hazardous environment for detecting the presence and/or amount of a volatile, combustible, and/or toxic gas within the hazardous environment. For example, the gas may be, but is not limited to, acetone, benzene, butadiene, butane, ethane, ethanol, ethylene, hexane, hydrogen, isobutanol, isopropyl alcohol, methane, methanol, methyl ethyl ketone (MEK), pentane, propane, propylene, toluene, xylene, and/or the like.

In applications where a volatile and/or combustible gas may be present, the gas detector assembly 110 may include intrinsic safety (IS) circuitry and housing. IS circuitry and housing may be designed to reduce the likelihood of an explosion and/or partially contain an explosion. Accordingly, IS circuitry may include electronic components for limiting current, voltage, and/or power. IS circuitry and/or components may also meet requirements relating to such as, but not limited to, the type of device, power rating, voltage rating, component spacing, component interconnect spacing, trace thickness, trace width, and/or the like. In some circumstances, IS component(s) are required to be segregated from non-IS component(s).

The detector 114 may include an interior chamber 111 that is hermetically sealed to separate a volume of space within the detector housing 120 from the environment 122. For example, in the illustrated embodiment, the detector 114 has an explosion-resistant detector housing 120 having an interior chamber 111 that holds the detector transceiver 118 and controller 116. The interior chamber 111 is separated from the environment 122 such that any combustion and/or explosion within the interior chamber 111 is less likely to extend into the environment 122. As such, any combustion and/or explosion that occurs within the interior chamber 111 is less likely to cause any substance within the environment 122 to combust and/or explode. The illustrated embodiment of the detector 114 may be commonly referred to as an "explosion-proof transmitter."

The detector 114 may include power supply component(s) and/or communication components (not shown; e.g., electrical wires and/or cables, circuit boards, other electrical pathways, switches, replays, communication notes, and/or the like). The power supply component(s) may provide power to the gas sensor 112 and/or the communication components. The detector 114 may hold one or more processing components (not shown; e.g., computers, processors, controllers, microprocessors, circuit boards, microcontrollers, memories, integrated circuits, and/or the like) that process signals from the gas sensor 112 that represent the parameter(s) sensed by the gas sensor 112. Processing of signals from the gas sensor 112 optionally includes data logging operations. The processing components includes the controller 116 which converts signals representing the parameter(s) sensed by the gas sensor 112 to desired engineering values to the detector transceiver 118.

The detector transceiver 118 transmits information received from controller 116 upstream to other devices. For example, in an embodiment, the detector transceiver 118 may transmit information to a wireless network via a wireless link. The wireless link can be any of a variety of protocols, including, but not limited to, Industry Standards Association (ISA) 100.11a, 802.11, Wifi, Zigbee, Bluetooth, Infrared Data Association (IrDA), wireless highway addressable remote transducer (HART) and/or the like. As used herein the HART protocol includes the specifications in the "HART Protocol Specifications" and are hereby incorporated by reference. HART Protocol Specifications [online]. HART Communications Foundation, 2013 [retrieved on Sep. 20, 2013]. Retrieved from the Internet: <URL: http://www.hartcomm.org/hcf/documents/documents_speclist.html>. As used herein the IrDA protocol includes the specifications in the "IrDA Core Specifications" and are hereby incorporated by reference. IrDA Core Specifications [online]. Infrared Data Association, 2011 [retrieved on Sep. 20, 2013]. Retrieved from the Internet: <http://irdajp.info/corespecs.html>. The wireless network may distribute the information received from the detector transceiver 118 to one more local or remote alarms, one or more local or remote monitoring stations, and/or the like.

The detector housing 120 may include a detector window 124. The detector window 124 is configured to provide a display and/or a communications access point. For example, the detector window 124 may include one or more user interface components 126 including, but not limited to, light emitting diodes (LED), liquid crystal display, and/or the like. The detector window 124 may provide an access point for a line of sight communications to exchange data with other devices. In the illustrated embodiment, the detector window 124 includes a detector transceiver 118. The detector transceiver 118 may use infrared (IR) light to provide line of sight communication. For example, the detector transceiver 118 may be configured a detector IR transceiver 128 configured with one or more IR light emitting diode (LED; not shown). Accordingly, the detector IR transceiver 128 is configured to bi-directionally exchange data using the IrDA protocol based data with another device, as discussed in detail below. As used herein, bi-directional data transfer may include, but is not limited to, transmitting and receiving data.

Figure 2:
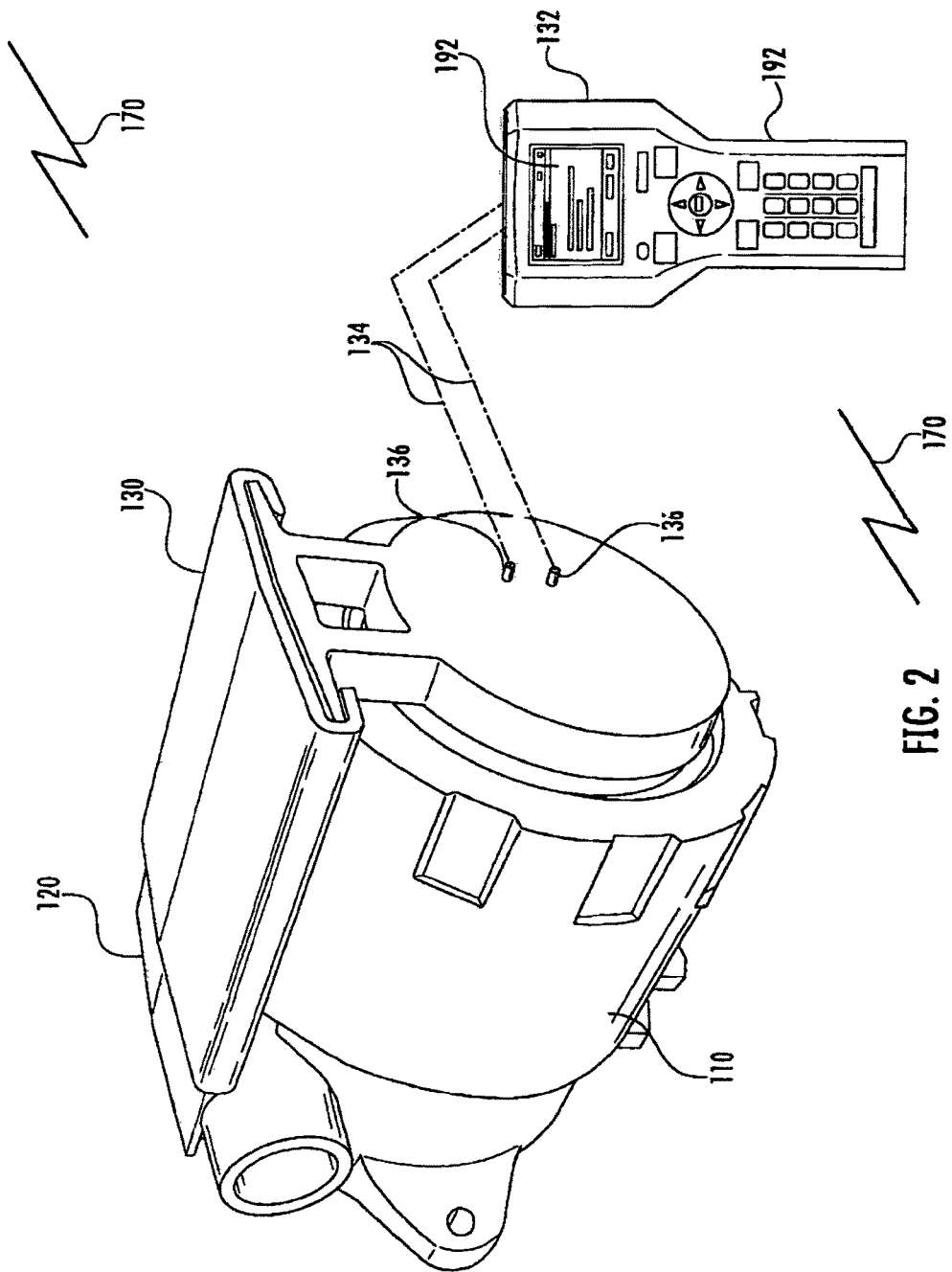
FIG. 2 is an illustration of an embodiment of a protocol converter module mounted to the gas detector assembly of FIG. 1 connected to a handheld device.
Figure 5:
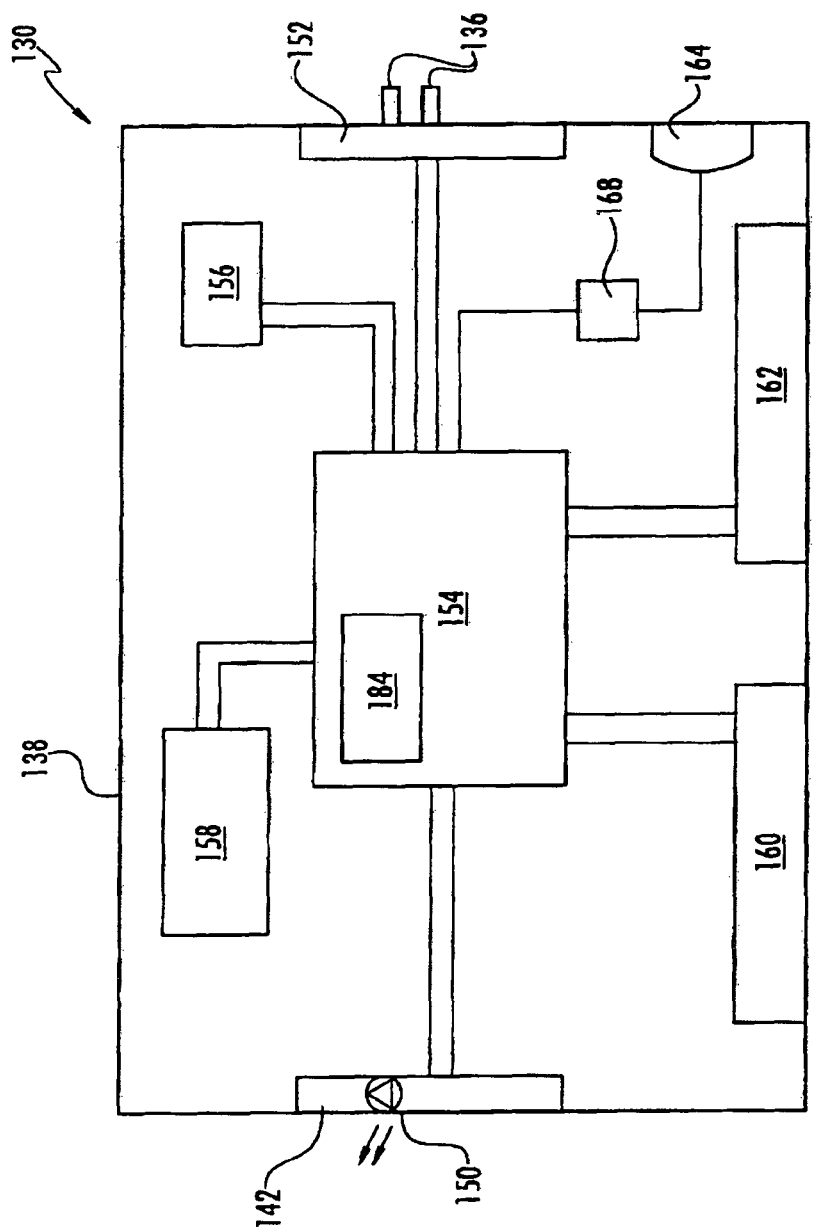
FIG. 5 is a system diagram of exemplary components housed within the converter module of FIG. 2.

FIG. 2 is an illustration of an embodiment of a protocol converter module 130 that is mounted to the gas detector assembly 110. The components within the protocol converter module 130 are illustrated in FIG. 5. The protocol converter module 130 is connected to an external device 132. As is discussed in detail below, the protocol converter module 130 is securely mounted to the detector housing 120. In the illustrated embodiment, the external device 132 is a handheld device; however, the external device 132 may be any computing device. For example, the external device 132 may be an Emerson® 475 Field Communicator, which is commercially available from Emerson® Electronics Company of Saint Louis, Mo. As is discussed below, the external device 132 is configured to exchange data with the protocol converter module 130 via the communication wiring 134 and/or a wireless radio frequency (RF) link 170.

The protocol converter module 130 exchanges data bi-directionally between the external device 132 and the gas detector assembly 110. The protocol converter module 130 receives, converts, and transmits data from the external device 132 to the gas detector assembly 110. Additionally, the protocol converter module 130 receives, converts, and transmits data from the gas detector assembly 110 to the external device 132. For example, the external device 132 may transmit data containing operating instructions to the protocol converter module 130. The protocol converter module 130 may then convert and transmit the data to the gas detector assembly 110, as described below. Operating instructions may include instructions relating to the operation of the sensor, such as for example, the time of day, the frequency of which samples are taken and/or the like. As another example, the operating instruction may include a command directing the gas detector assembly 110 to transmit data representing a log file containing information recorded by the gas detector assembly 110. The gas detector assembly 110 may then transmit the data to the protocol converter module 130. The protocol converter module 130 may then reformat the data and transmit the data to the external device 132.

The protocol converter module 130 allows the external device 132 to interact indirectly (e.g., through the protocol converter module 130) with the gas detector assembly 110. In an embodiment, the interaction allows the external device 132 to provide a user interface for the gas detector assembly 110. For example, in various embodiments, the gas detector assembly 110 does not include the user interface components 126. A gas detector assembly 110 that does not include the user interface components 126 is often referred to as a "blind" detector. Accordingly, the protocol converter module 130 allows the external user interface 192 on the external device 132 to interact with the gas detector assembly 110. Data collected from the user interface 192 can be sent to the gas detector assembly 110 via the protocol converter module 130. Conversely, data from the gas detector assembly 10 may be presented on the user interface 192 via the protocol converter module 130.

With reference to FIG. 5, the protocol converter module 130 include a first converter transceiver 142 configured to bi-directionally exchange data with the gas detector assembly 110 and a second converter transceiver 152 configured to bi-directionally exchange data with the external device 132. The first converter transceiver 142 may include an IR transceiver 188. The IR transceiver 188 may include one or more IR LED(s) (shown in FIG. 5) to communicate with the detector transceiver 118. The second converter transceiver 152 may include an I/O transceiver 186. The I/O transceiver 186 communicates serially with the external device 132 via an intrinsically safe input/output (IS I/O) connector 136 that mates with the communication wiring 134. The first converter transceiver 142 may utilize a first protocol and the second converter transceiver 152 may utilize a second protocol that is different from the first protocol. For example, the data exchanged between the external device 132 and the protocol converter module 130 may be formatted according to a first protocol, whereas the data exchanged between the protocol converter module 130 and the gas detector assembly 110 may be formatted according to a second protocol that is different from the first protocol. Thus, in an embodiment, the protocol converter module 130 is configured to convert data from the first protocol to the second protocol, and the control module 130 is configured to convert data from the second protocol to the first protocol.

An electronic converter 154 held within converter housing 138 interacts with the first converter transceiver 142 and the second converter transceiver 152 to convert data from one format to the other. For example, in the illustrated embodiment, protocol converter module 130 exchanges data with the gas detector assembly 110 using the IrDA protocol, and the protocol converter module 130 exchanges data with the external device 132 using the HART protocol. Thus, the electronic converter may convert (e.g., translate) data received from gas detector assembly 110 utilizing the IrDA protocol via the first converter transceiver 142 and transmit the data received from the gas detector assembly 110 to the external device 132 utilizing the HART protocol via the second converter transceiver 152.

The converter housing 138 includes the IS input/output (I/O) connectors 136. The I/O connectors 136 may be used to establish wired HART communications with the external device 132. Wired HART communications typically include a circuit having a time varying current ranging from 4 mA to 20 mA carried over a twisted pair wire. A power supply (not shown) and/or a master host (e.g., a computer; not shown) may provide the current in the circuit. Wired HART communications make use of frequency shift keying (FSK) to superimpose digital communication signals in the varying current. The I/O connectors 136 are used to allow the protocol converter module 130 to join the circuit along with the external device 132 and/or any other wired HART compatible device.

The I/O connectors 136 interface with the second converter transceiver 152 to provide an intrinsically safe electrical access point to communicate with the protocol converter module 130. Optionally, the I/O connectors 136 interface with the I/O transceiver 186. In the illustrated embodiment, the I/O connectors 136 are shown as exposed pins, but the I/O connectors 136 may be any other pin type of array and/or any other type of connector mechanism. The I/O connectors 136 may regulate one or more of, power rating, voltage rating, component spacing, component interconnect spacing, trace thickness, trace width, and/or the like to maintain an intrinsically safe electrical connection.

Optionally, the protocol converter module 130 may exchange data with the external device 132 via the wireless RF link 170. The wireless RF link 170 may be any wireless link and may employ any of a variety of protocols including, but not limited to, ISA 100.11a, wireless HART, Wifi, and/or the like.

Once mounted to the gas detector assembly 110, the protocol converter module 130 may transmit and receive data with the gas detector assembly 110. The data transmitted may include, but is not limited to, operating instructions, operating files, and/or the like. Operating instructions may include, but are not limited to, logging start/stop instructions, logging interval instructions, logging duration, and/or the like. Operating files may include, but are not limited to executable software, firmware, and/or the like. The data transmitted may include, but is not limited to, log files, system status, and/or the like. Log files may include at least one of a history of sensor readings, gas concentrations in a surrounding area over a predetermined period of time, and information regarding operating states and/or status of the detector assembly over a predetermined period of time. System status may include information relating to sensor life, activation time, battery life and/or the like. The data may be transmitted from the first converter transceiver 142 to the detector transceiver 118 via an infrared link and formatted in the IrDA protocol.

Once mounted to the gas detector assembly 110, the protocol converter module 130 may interface with the external device 132. The communication wiring 134 may be used to connect the I/O connectors 136 to the external device 132 to form a complete transmission loop (e.g., a complete circuit). Once connected, the protocol converter module 130 may bi-directionally exchange data using the HART protocol.

Figure 3:
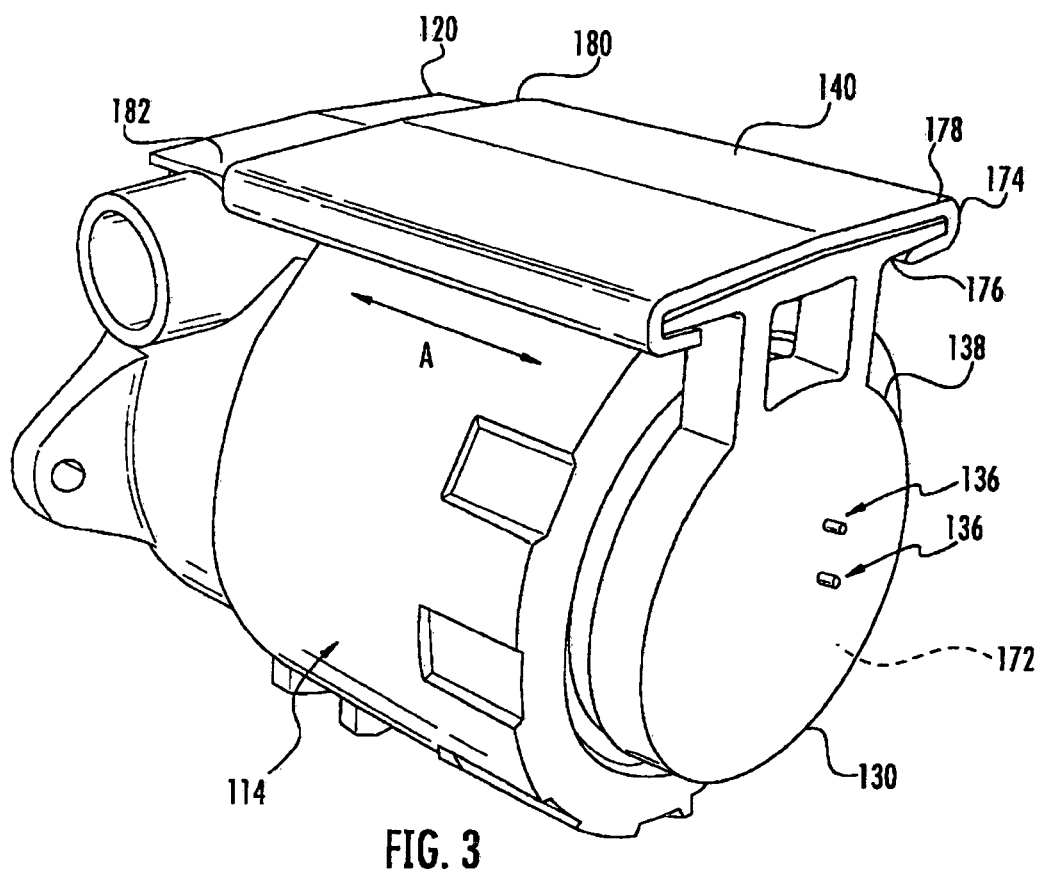
FIG. 3 is a perspective view of the converter module of FIG. 2 mounted to the detector housing of the detector of FIG. 2.

FIG. 3 is a perspective view of the protocol converter module 130 removably mounted to the detector housing 120 of the detector 114. The protocol converter module 130 includes a converter housing 138. The converter housing 138 has an interior chamber 172 that may be hermetically sealed to separate a volume of space within the converter housing 138 from the environment 122. For example, in the illustrated embodiment, the protocol converter module 130 has an explosion-resistant converter housing 138. The interior chamber 172 is separated from the environment 122 such that any combustion and/or explosion that occurs within the interior chamber 172 is less likely to cause any substance within the environment 122 to combust and/or explode. The illustrated embodiment may be commonly referred to as an "IS housing."

The converter housing 138 mates with a converter mount 140. The converter mount 140 is configured to mate with the converter housing 138 at a first end 178 of the converter mount 140. The protocol converter module 130 may mount to the converter mount 140 by sliding the rail structure 176 of the converter housing 138 along and into the u-shaped structure 174 on the first end 178 of the converter housing 138. The converter mount 140 also includes a shape (not shown) on the second end 180 that is complementary to the mounting portion 182 of the detector housing 120. The converter mount 140 mates with the detector housing 120 by providing a friction fit between the detector housing 120 and the converter mount 140. Additionally or alternatively, the converter mount 140 and/or the converter housing 138 may use any other mounting strategy for mounting the protocol converter module 130 to the detector housing 120, such as, but not limited to, an adhesive, an retaining device, a snap-fit, a latch, a clip, a clamp, a threaded fastener, and/or the like.

When securely mounted, the protocol converter module 130 remains rigidly fixed to the detector housing 12, such that line of sight communication with the detector transceiver 118 and a first converter transceiver 142 housed within the converter housing 138 is maintained. Line of sight communication between the detector transceiver 118 and the first converter transceiver 142 is discussed in detail below. Further, when mounted, independent movement between the protocol converter module 130 and the detector housing 120 is reduced. Additionally, the converter mount 140 is configured to be releasably detached from the detector housing 120. The converter mount 140 may be removed from the converter housing 138 by sliding the converter mount 140 in the direction of arrow A longitudinally along the rail structure 176. Similarly, the converter mount 140 may be detached from the mounting portion 182.

Figure 4:
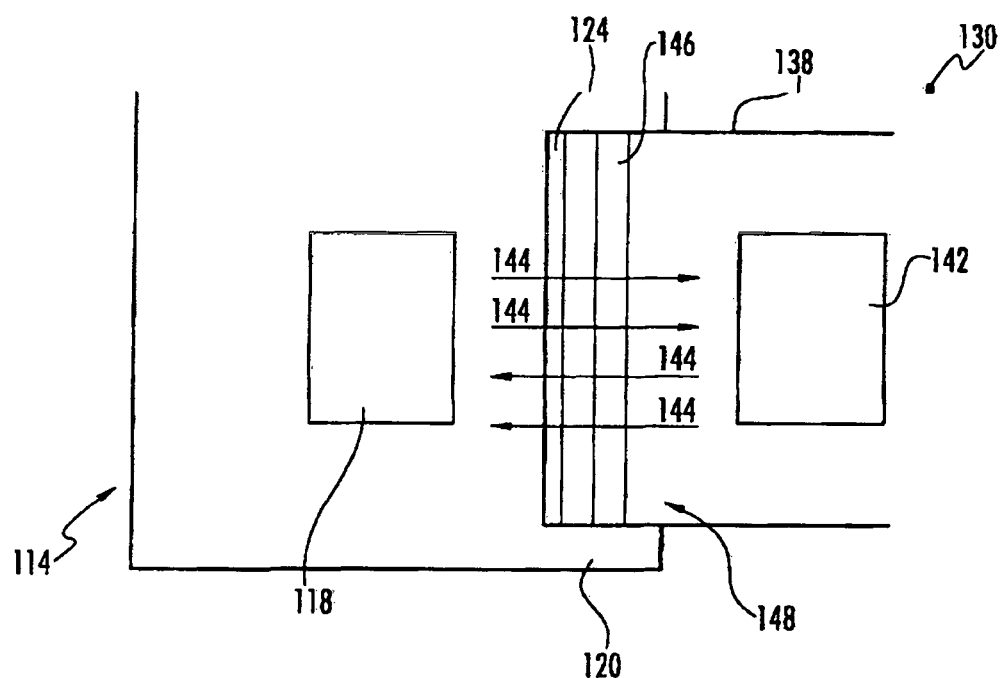
FIG. 4 is an illustration of a cut-away elevation view of the converter module mounted to the detector shown in FIG. 2.

FIG. 4 is an illustration of a cut-away elevation view of the protocol converter module 130 mounted to the detector housing 120 of the detector 114 using the converter mount 140 (not shown). The converter housing 138 includes a mating interface 148 having a converter window 146. The converter window 146 is a transparent window configured to allow the light waves 144 to travel through the converter window 146. The converter window 146 is configured to align with the detector window 124 such that when the mating interface 148 interlocks with the detector window 124, the first converter transceiver 142 within the converter housing 138 aligns with the detector IR transceiver 128 within the detector window 124. As shown in the illustrated embodiment, the light rays 144 representing infrared light are permitted to traverse the detector window 124 and converter window 146 to travel to and from the first converter transceiver 142 and the detector transceiver 118.

Optionally, the mating interface 148 is sized and shaped to conform to the size and shape of the detector housing 120. Additionally or alternatively, the detector housing 120 may include a key component (not shown; e.g., a protrusion) that interlocks and/or interacts with a groove component (not shown) on the converter housing 138 to encourage alignment between the detector window 124 and the converter window 146.

FIG. 5 is a system diagram of exemplary components held within the converter housing 138. The electronic converter 154 may include a microprocessor 184 configured to convert data between the first protocol and the second protocol. The electronic converter 154 described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as the microprocessor 184, processors, controllers, or the like. These devices may be off-the-shelf devices that perform the operations described herein from the instructions described above. Additionally or alternatively, one or more of these devices may be hard-wired with logic circuits to perform these operations.

The protocol converter module 130 includes the electronic converter 154 that controls the data exchange and various protocol conversion operations. The electronic converter 154 includes the microprocessor 184, or equivalent circuitry, designed specifically for exchanging data and protocol conversion operations and may further include RAM or ROM memory, logic and timing circuitry, state machine circuitry, and I/O circuitry. The electronic converter 154 includes the ability to process or monitor signals (data) as controlled by a program code stored in memory. The details of the design and operation of the electronic controller 154 are not critical to the present invention. Rather, any suitable electronic converter 154 may be used. Among other things, the electronic converter 154 receives data from the first converter receiver and the second converter receiver and converts the data from the first protocol to the second. The electronic converter also sends data to the first converter receiver and the second converter receiver. For example, the first protocol may include the IrDA protocol and the second protocol may include the serial HART protocol.

The block diagrams of embodiments herein illustrate various blocks labeled "module". It is to be understood that the modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

The converter housing 138 holds the first converter transceiver 142. The electronic converter 154 is operably connected to the first converter transceiver 142. The converter housing 138 holds the second converter transceiver 152. The electronic converter 154 is operably connected to the second converter transceiver 152. As an example of data flow through the protocol converter module 130, the first converter transceiver 142 may receive data from the detector transceiver 118 formatted in the IrDA protocol. The data may flow to the electronic converter 154 which converts (e.g., translates) the data to serial HART protocol. The data may then be transmitted to the external device 132 via the second converter transceiver 152. As another example, data may be received by the second converter transceiver 152 serially and formatted in the HART protocol. The data may then flow to the electronic converter 154 that converts the data to the IrDA protocol. The data may then be transmitted to the detector transceiver 118 via the first converter transceiver 142.

The protocol converter module 130 includes a memory 156, within the converter housing 138. The memory 156 may be used to cache and/or buffer data received from the first converter transceiver 142 and/or the second converter transceiver 152. For example, the electronic converter 154 may receive data from the first converter transceiver 142 and store the received information in the memory 156 as a log file, a system file, a temporary file (e.g., files containing transient information), and/or the like. Log files may include at least one of a history of sensor readings, sensor life, gas concentrations in a surrounding area over a predetermined period of time, and information regarding operating states and/or status of the detector assembly over a predetermined period of time, a history of process data, calibration data, and/or user information. User information may include, but is not limited to, identifiers that indicate the operating entity, the location, and/or the date of installation of the gas detector assembly 110. Additionally or optionally, the memory 156 may include predetermined operating system commands that are sent to the detector 114 as discussed below.

The protocol converter module 130 includes a first magnetically actuated switch (MAS) 160 within the converter housing 138. The first MAS 160 provides an IS interface (e.g., provides a switch that is not exposed to the environment 122) to allow a user to interact with the converter module 10. The first MAS 160 is communicability coupled to the electronic converter 154. The first MAS 160 may be actuated to enter select states by the application or removal of a magnetic field. Select states for the first MAS 160 may include, but are not limited to, an engaged and a disengaged state. As one option, the external device 132 may include a complementary handheld MAS 190 (not shown) housed within the external device 132 to interact with the first MAS 160. For example, the handheld MAS 190 may be placed an upright orientation to cause the first MAS 160 to enter the engaged state. Alternatively, the handheld MAS 190 may be placed in an up-side down orientation to cause the first MAS 160 to enter the disengaged stated. As an option, the first MAS 160 may be configured to instruct the electronic converter 154 to transmit predetermined operating instructions via the first converter transceiver 142 to the detector 114 upon entering the engaged state. Predetermined operating instructions may include, but are not limited, to uploading transmitter firmware, software, and/or the like. Although a magnetic switch is used in the illustrated embodiment, any other type of switch may be used.

Additionally, the protocol converter module 130 may include a second MAS 162. The second MAS 162 may include the same or different operating states (e.g., engaged and/or disengaged) as the first MAS 160. The second MAS 162 is communicability coupled to the electronic converter 154. When triggered to enter the engaged state, the second MAS 162 may be configured to instruct the electronic converter 154 to download (e.g., transmit from the protocol converter module 130 to the external device 132 via the second converter transceiver 152) a log file stored in the memory 156.

Optionally, the protocol converter module 130 may include an auxiliary communication port 164. The auxiliary communication port 164 may be configured to exchange data with the external device 132 using a third protocol that is different from the first protocol and the second protocol. For example, in the illustrated embodiment, the auxiliary communication port 164 is configured as a universal serial bus (USB) port, however any connection strategy may be used. The auxiliary communication port 164 may include the IS circuitry module 168 configured to ensure the connection between the auxiliary communication port 164 and the electronic converter 154 remains IS. The IS circuitry module 168 may include, but is not limited to, electronic components for limiting current, voltage, and/or power. The IS circuitry module 168 may also include a low-dropout voltage regulator, a fuse, and/or the like.

The protocol converter module 130 includes an intrinsically safe power module (ISPM) 158 within the converter housing 138 configured to provide electrical energy to the electronic components housed within the converter housing 138, including but not limited to, the electronic converter 154, the first converter transceiver 142, the second converter transceiver 152, the first MOS 160, the second MOS 162, the auxiliary communication port 164 and/or the memory 156. The ISPM 158 includes circuitry and/or traces such that an intrinsically safe electrical path is maintained. The ISPM 158 may include at least one of a low-dropout voltage regulator, a fuse, or a battery. Additionally or optionally, the ISPM 158 may supply electrical power to the memory 156, the first converter transceiver 142, the second converter transceiver 152, the auxiliary communication port 164 and/or the like.

Figure 6:
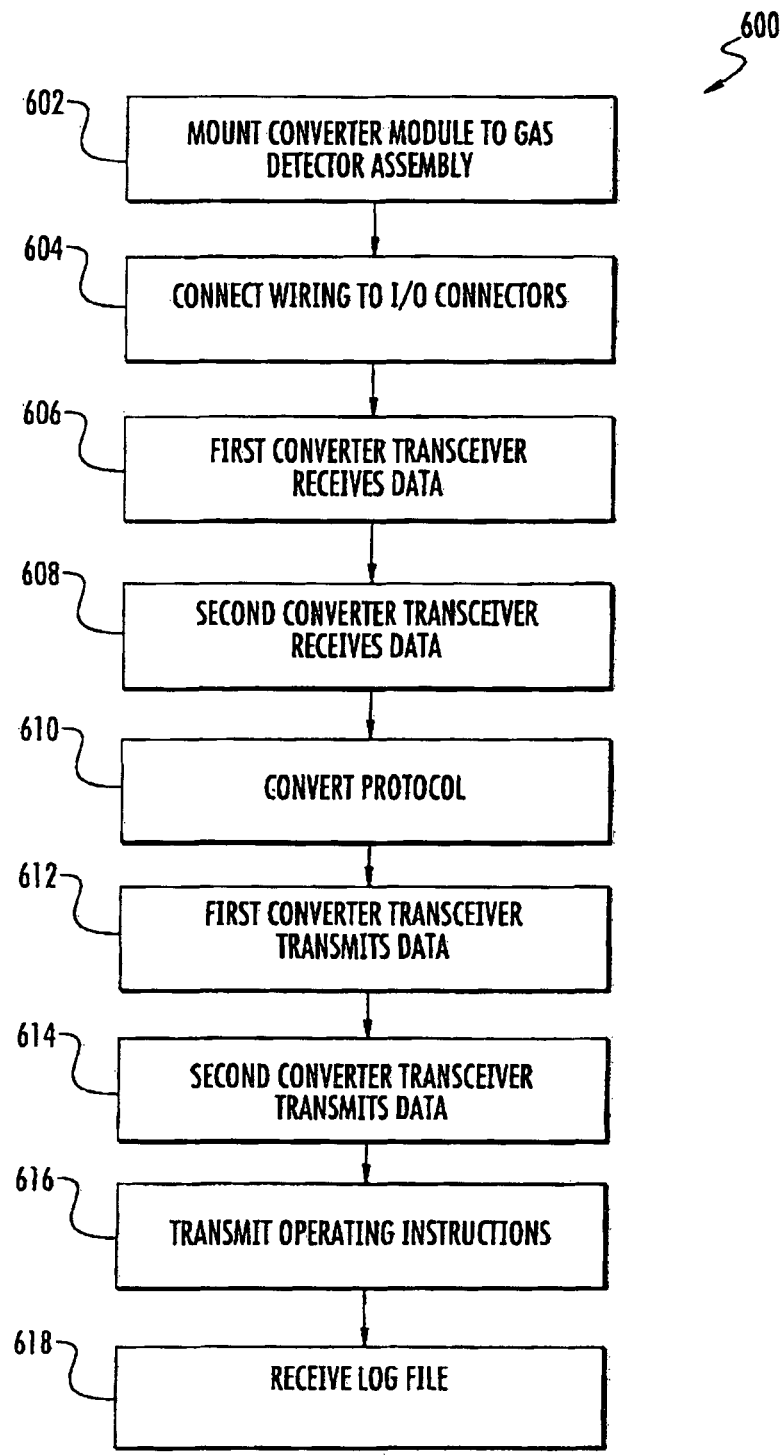
FIG. 6 is a flowchart of an exemplary embodiment of a method for bi-directionally exchanging data with a gas detector assembly and an external device using one or more of the embodiments described herein.

FIG. 6 is a flowchart of an exemplary embodiment of a method for bi-directionally exchanging data with a gas detector assembly and an external device using one or more of the embodiments described herein.

The method 600 begins at 602 by securely mounting the protocol converter module 130 to the gas detector assembly 110. The converter mount 140 is used to mount the protocol converter module 130 to the gas detector assembly 110. The protocol converter module 130 is mounted to the converter mount 140 by sliding the rail structure 176 of the converter housing 138 along and into the u-shaped structure 174 on the first end 178 of the converter housing 138. The converter 130 and the converter mount 140 are then mounted to the detector housing 120. The detector housing 120 includes a mounting portion 182 that is complementary to the second end 180 of the converter mount 140. The converter mount 140 is mated with detector housing 120 by a friction fit. Optionally or additionally, additional securing means may be used to mount the protocol converter module 130 to the gas detector assembly 110. Additional securing means may include, but are not limited to, an adhesive, an retaining device, a snap-fit, a latch, a clip, a clamp, a threaded fastener, and/or the like. Optionally, the method may position the converter mount 140 in a fixed location relative to the first converter transceiver 142 such that the first converter transceiver 142 is located at a known position relative to the detector transceiver 118 when the converter housing 138 is securely mounted to the detector housing. Optionally or additionally, the method may align the mating interface 148 such that the transparent converter window 146 aligns with the transparent detector window 124. Additionally, when aligned, the first converter transceiver 142 forms line of sight communication with the detector transceiver 118. After the protocol converter module 130 is mounted to the gas detector assembly 110, the method may proceed to 604.

At 604, the method connects the communication wiring 134 to the I/O connectors 136. The communication wiring 134 may be connected to the I/O connectors 136 using any type of connector to form an electrical connection. Once connected, the protocol converter module 130 may communicate using the serial HART protocol to other devices including via the communication wiring 134, but not limited to, the external device 132.

At 606, the first converter transceiver 142 may receive data from the detector transceiver 118 formatted in the first protocol. In an embodiment, the first protocol represents the IrDA protocol. After the first converter transceiver 142 receives the data, the first converter transceiver 142 passes the data to the electronic converter 154. In other words, the data flows from the first converter transceiver 142 to the electronic converter 154. After the electronic converter 154 receives the data, the method may proceed to 608.

At 608 the second converter transceiver 152 may receive data from the external device 132 formatted in the second protocol. In an embodiment, the second protocol represents the serial HART protocol. After the second converter transceiver 152 receives the data, the second converter transceiver 152 passes the data to the electronic converter 154. After the electronic converter 154 receives the data, the method may proceed to 610.

At 610, the electronic converter 154 converts (e.g., translates, reformats, and/or the like) the data received from the first converter transceiver 142 and formatted in the first protocol to data formatted in the second protocol. For example, the electronic converter 154 may convert the data from the IrDA protocol to the HART protocol. After the data are converted, the data may flow from the electronic converter 154 to the second converter transceiver 152. Similarly, the electronic converter 154 converts data received from the second converter transceiver 152 and formatted in the second protocol to data formatted in the first protocol. For example, the electronic converter 154 may convert the data from the HART protocol to the IrDA protocol. After the data are converted, the data may flow from the electronic converter 154 to the first converter transceiver 142. The method may then continue to 612.

At 612, the first converter transceiver 142 may transmit the data received from the electronic converter 154 to the detector transceiver 118. After the data are transmitted, the method may continue to 614.

At 614, the second converter transceiver 152 may transmit the data received from the electronic converter 154 to the external device 132 via the I/O connector 136 and the communication wiring 134.

Optionally, at 616, the electronic converter 154 may transmit operating instructions to the detector 114. As one option, the external device 132 may actuate the first MAS 160 by changing the orienting the handheld MAS 190 to cause the first MAS 160 to enter an engaged state. After the first MAS 160 enters the engaged state, the electronic converter 154 may transmit predetermined operating instructions via the first converter transceiver 142 to the detector 114 upon entering the engaged state. Predetermined operating instructions may include, but are not limited, to uploading transmitter firmware, software, and/or the like.

Optionally, at 618 the electronic converter 154 may receive data representing a log file. As one option, the external device 132 may actuate the second MAS 162 by changing the orienting the handheld MAS 190 to cause the second MAS 162 to enter an engaged state. When triggered to enter the engaged state, the second MAS 162 may be configured to instruct the electronic converter 154 to download (e.g., transmit from the protocol converter module 130 to the external device 132 via the second converter transceiver 152) a log file stored in the memory 156.

By practicing one or more of the embodiments described herein, a converter module may be used communicably connect a handheld communicator that uses a serial HART protocol to a gas detector that uses IrDA protocol.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter described herein without departing from its scope. While the dimensions and types of materials described herein are intended to define the parameters of the subject matter described herein, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the subject matter described herein, including the best mode, and also to enable any person skilled in the art to practice the embodiments of the subject matter described herein, including making and using any devices or systems and performing any incorporated methods. The patentable scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A protocol converter module for use with a gas detector assembly having gas sensor, controller, and a detector transceiver housed within an intrinsically safe detector housing, the converter module comprising:

a converter housing having a converter mount configured to securely mount the converter module to the detector housing, the converter housing including a mating interface having a transparent converter window that is configured to align with a transparent detector window provided in the detector housing, the first converter transceiver positioned to align with the converter window such that, when the converter housing is mounted on the detector housing, the first converter transceiver forms line of sight communication with the detector transceiver;

a first converter transceiver, within the converter housing, configured to bi-directionally exchange data with the detector transceiver utilizing a first protocol;

a second converter transceiver, within the converter housing, configured to bi-directionally exchange data with an external device utilizing a second protocol; and an electronic converter, within the converter housing, coupled to the first and second converter transceivers and configured to convert the data between the first and second protocols, the electronic converter configured to allow data collected from an external user interface on the external device to be sent to the gas detector assembly.

2. The converter module of claim 1, wherein the first converter transceiver is an infrared (IR) transceiver configured to communicate through line of sight with an IR transceiver in the detector housing and the second converter transceiver is an input/output (I/O) transceiver configured to communicate serially with the external device.

3. The converter module of claim 1, wherein the first protocol utilizes infrared light to communicate data to and from the detector transceiver.

4. The converter module of claim 1, wherein the first protocol represents an Infrared Data Association (IrDA) protocol.

5. The converter module of claim 1, wherein the second protocol represents a serial highway addressable remote transducer (HART) protocol.

6. The converter module of claim 1, wherein the converter mount is positioned in a fixed location relative to the first converter transceiver such that the first converter transceiver is located at a known position relative to the detector transceiver when the converter housing is securely mounted on the detector housing.

7. The converter module of claim 1, wherein the second protocol represents a wireless radio frequency (RF) link for wireless communication with an external HART communicator device.

8. The converter module of claim 1, further comprising an electronically intrinsically safe I/O connector, provided on the converter housing, configured to couple the external device to the second converter transceiver.

9. The converter module of claim 1, further comprising a first magnetically actuated switch held within the converter housing, wherein the first magnetically actuated switch is configured to instruct the electronic converter to transmit predetermined operating instructions via the first converter transceiver to the detector when the external device triggers the first magnetically actuated to enter a select state.

10. The converter module of claim 1, further comprising memory, within the converter housing, configured to download a log file from the detector assembly, the log file including at least one of a history of sensor readings, gas concentrations in a surrounding area over a predetermined period of time and information regarding operation states and status of the detector assembly over a predetermined period of time.

11. The converter module of claim 10, further comprising a second magnetically actuated switch within the converter housing, wherein the second magnetically actuated switch is configured to instruct the electronic converter to download the log file in the memory when the external device triggers the second magnetically actuated switch to enter a select state.

12. The converter module of claim 1, wherein the converter mount is detachable from the detector housing.

13. The converter module of claim 1, wherein the electronic converter further includes a microprocessor configured to convert the data between the first and second protocols.

14. The converter module of claim 1, further comprising an intrinsically safe power module (ISPM) held within the converter housing and is configured to provide electrical energy to the electronic converter, the ISPS having at least one of a low-dropout voltage regulator, a fuse, or a battery.

15. A method of bi-directionally exchanging data with a gas detector assembly and an external device comprising:

securely mounting a protocol converter module having a converter housing to the gas detector assembly using a converter mount, the converter housing including a mating interface having a transparent converter window and securely mounting the protocol converter to the gas detector assembly includes aligning the transparent converter window with a transparent detector window provided in the detector housing such that the first converter transceiver forms line of sight communication with the detector transceiver;

bi-directionally exchanging data with a detector transceiver housed in the gas detector assembly using a first converter transceiver housed in the converter housing utilizing a first protocol;

bi-directionally exchanging data with the external device using a second converter transceiver housed in the converter housing utilizing a second protocol;

converting the data between the first and second protocols using an electronic converter communicably coupled to the first and second converter transceivers; and allowing data collected from an external user interface on the external device to be sent to the gas detector assembly.

16. The method of claim 15, wherein the first protocol represents an Infrared Data Association (IrDA) protocol.

17. The method of claim 15, wherein the second protocol represents a serial highway addressable remote transducer (HART) protocol.

18. The method of claim 15, wherein the second protocol represents a wireless radio frequency (RF) link for wireless communication with the external device.

19. The method of claim 15, wherein bi-directionally exchanging data with the detector transceiver further comprises downloading a log file from the detector transceiver to a memory module housed within the converter module, the log file including at least one of a history of sensor readings, gas concentrations in a surrounding area over a predetermined period of time or information regarding operation states and status of the detector assembly over a predetermined period of time.

20. The method of claim 15, wherein bi-directionally exchanging data with detector transceiver further comprises transmitting predetermined operating instructions to the detector assembly, the predetermined operating instructions including at least one of logging start instructions, logging stop instructions, logging interval instructions, or logging duration.

21. The method of claim 15, wherein the mounting of the protocol converter to the gas detector assembly includes positioning the converter mount in a fixed location relative to the first converter transceiver such that the first converter transceiver is located at a known position relative to the detector transceiver when the converter housing is securely mounted to the detector housing.

22. The method of claim 15, further comprising actuating a first magnetically actuated switch held within the converter housing to instruct the electronic converter to transmit predetermined operating instructions via the first converter transceiver to the detector when the external device triggers the first magnetically actuated switch to enter a select state, the predetermined operating instructions including at least one of logging start instructions, logging stop instructions, logging interval instructions, or logging duration.

23. The method of claim 15, further comprising actuating a second magnetically actuate switch held within the converter housing to instruct the electronic converter to download a log file from the detector assembly, the log file including at least one of a history of sensor readings, gas concentrations in a surrounding area over a predetermined period of time or information regarding operation states and status of the detector assembly over a predetermined period of time.

* * * * *